United States Patent [19]
Esser

[11] Patent Number: 6,096,040
[45] Date of Patent: Aug. 1, 2000

[54] UPPER EXTREMITY BONE PLATES

[75] Inventor: Rene D. Esser, Saratoga, Calif.

[73] Assignee: Depuy Ace Medical Company, El Segundo, Calif.

[21] Appl. No.: 09/202,409

[22] PCT Filed: Jun. 13, 1997

[86] PCT No.: PCT/US97/10274

§ 371 Date: Dec. 14, 1998

§ 102(e) Date: Dec. 14, 1998

[87] PCT Pub. No.: WO97/47251

PCT Pub. Date: Dec. 18, 1997

Related U.S. Application Data

[60] Provisional application No. 60/019,932, Jun. 14, 1996.

[51] Int. Cl.[7] ................................... A61B 17/80
[52] U.S. Cl. .............................................. 606/69
[58] Field of Search ................. 606/60, 69–72, 606/74

[56] References Cited

U.S. PATENT DOCUMENTS

| | | | |
|---|---|---|---|
| 4,903,691 | 2/1990 | Heinl | 606/70 |
| 4,905,679 | 3/1990 | Morgan | 606/70 |
| 5,006,120 | 4/1991 | Carter | 606/69 |
| 5,197,966 | 3/1993 | Sommerkanp | 606/69 |
| 5,545,162 | 8/1996 | Huebner | 606/57 |
| 5,586,985 | 12/1996 | Putnam et al. | 606/69 |

FOREIGN PATENT DOCUMENTS 2622-431  5/1989  France .

OTHER PUBLICATIONS

Submitted "Treatment of Three–and Four–Part Fractures of the Proximal Humerus With a Modified Cloverleaf Plate," Journal of Orthopedic Trauma, vol. 8, No. 1, pp. 12–22, 1994.

Primary Examiner—Michael Buiz
Assistant Examiner—David O. Reip

[57] ABSTRACT

A bone plate is especially adapted to solve the problems pertinent to all fracture types of the proximal humerus but especially all three-part and four-part fractures and fracture dislocations of the proximal humerus. The first bone plate (30) is configured and arranged to match the contour of a healthy unfractured proximal humerus. The bone plate (30) includes an elongate shaft portion (32) and a head portion (34). The shaft portion (32) is adapted for receiving bone screws to fix the bone plate to a shaft of a humerus. The head portion includes a first head section (53) and a second head section (54), with an obtuse angle defined therebetween. The first and second head sections (53, 54) extend laterally away from a longitudinal axis of the shaft portion (32) in generally opposite directions. The second head section (54) is configured and arranged with lateral portion (86) to secure multiple fractures of a head of proximal humerus while extending laterally adjacent to the biceps tendon to preserve the tendon. First head section (53) forms an angled gap (61) relative to second head section (54) to avoiding impingement of the acromion process of the shoulder. Another pair of bone plates includes a bone plate especially adapted for fixing fractures on the dorsal side of the distal radius and a bone plate especially adapted for fixing fractures on the volar side of the distal radius. The bone plates are pre-shaped to match the contour of the anatomic shape of a dorsal side and a volar side, respectively, of an unfractured distal radius.

11 Claims, 6 Drawing Sheets

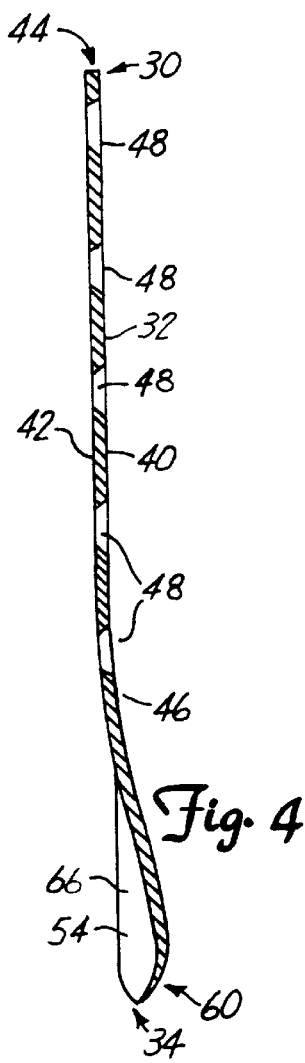
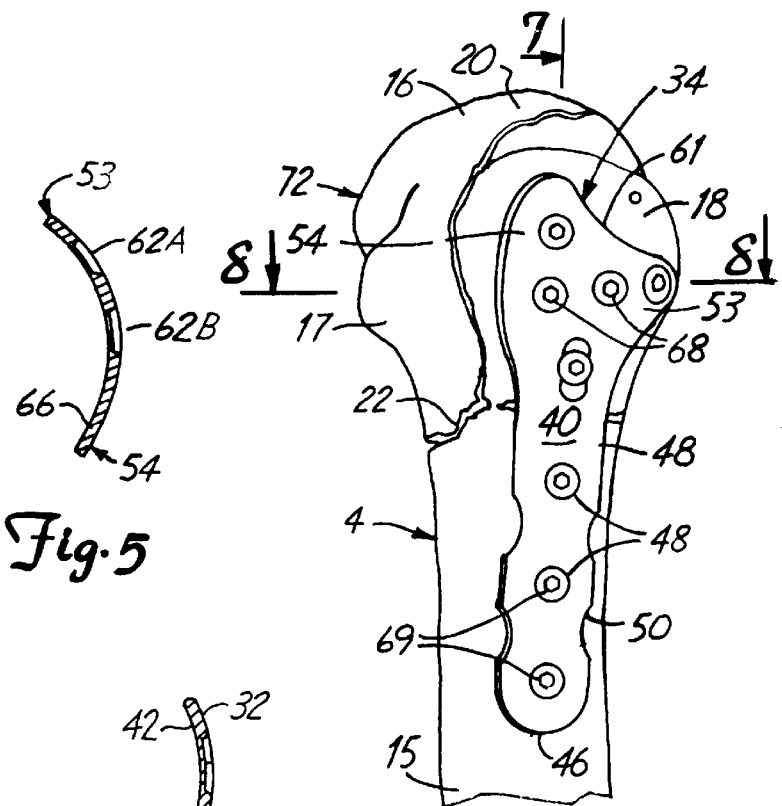
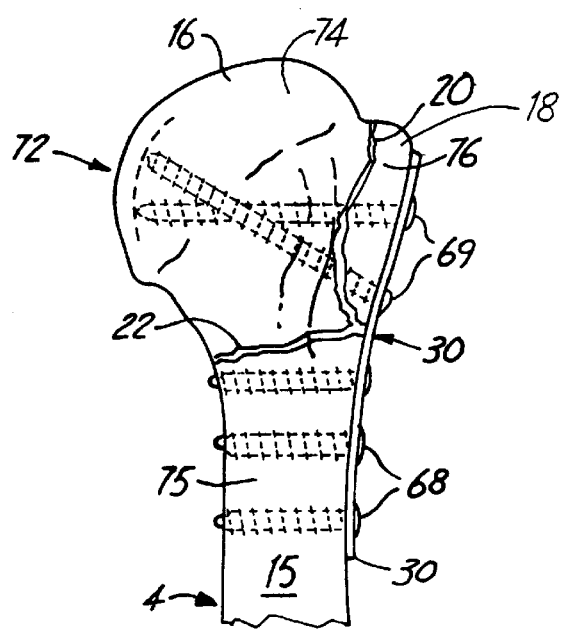
Fig. 4
Fig. 5
Fig. 5B
Fig. 6
Fig. 7

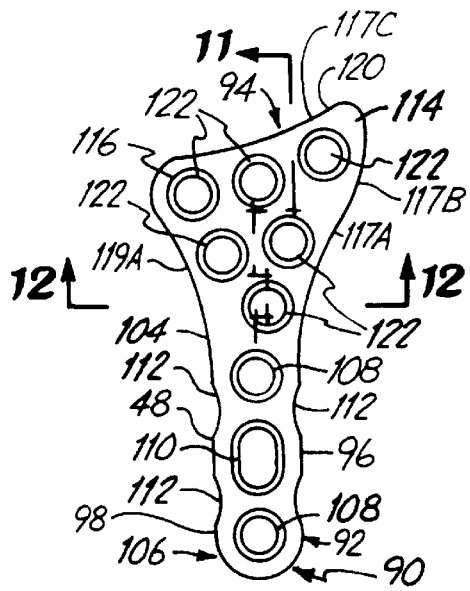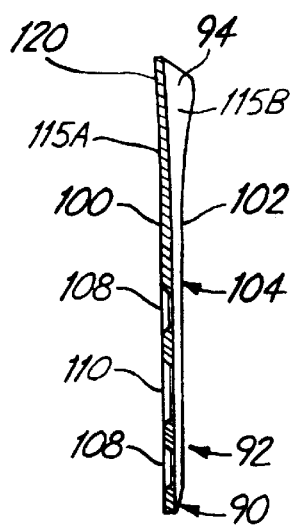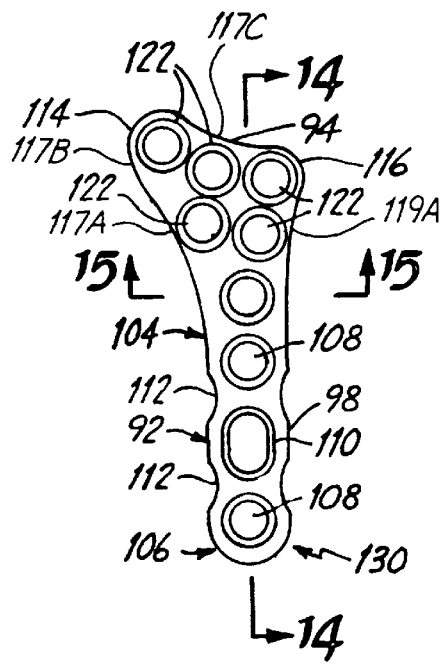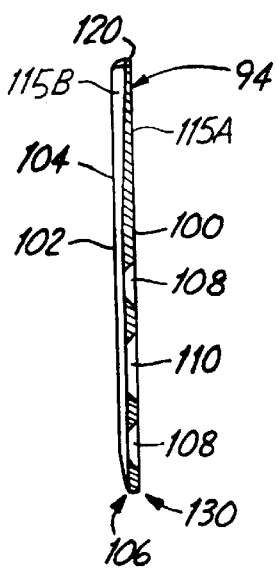

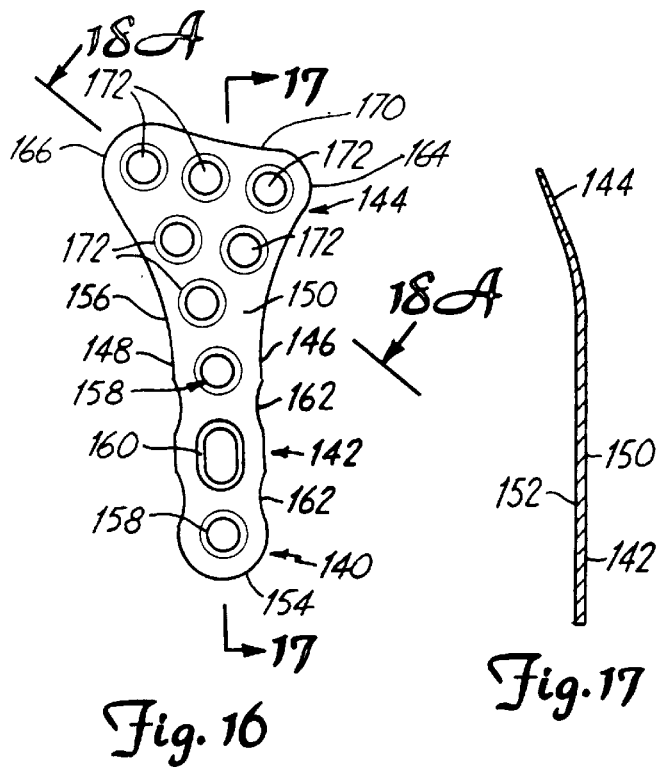

UPPER EXTREMITY BONE PLATES

CROSS-REFERENCES TO RELATED APPLICATIONS

This application is a U.S. national application of international application Ser. No. PCT/US97/10274 filed Jun. 13, 1997, which claims priority to U.S. provisional application Ser. No. 60/019,932 filed Jun. 14, 1996.

BACKGROUND OF THE INVENTION

The present invention relates to bone plates. In particular, the present invention relates to a bone plate for fixating fractures of a proximal humerus bone and a bone plate for fixating fractures of a distal radius bone.

The proximal humerus comprises the upper portion of the humerus, i.e. upper arm of the human body, commonly known as the shoulder area. Fractures of the proximal humerus typically result from traumatic injuries such as sporting accidents and can be more frequent with age due to bone loss. Fractures of the proximal humerus are treated by exposing the fracture site and reducing the bone fracture and then placing a plate or other means onto the bone to fixate the fracture for healing in the reduced position. Reducing the fracture includes realigning and positioning the fractured portions of the bone to their original position or similar stable position. Fixating the fracture includes positioning a plate over the fractured portions and securing the plate onto the fractured bones and adjacent nonfractured bones with bone screws.

Conventional fixation plates have several shortcomings when applied to the proximal humerus. First, the most common conventional plate used for fixating proximal humerus fractures is the AO T-plate which is not specifically adapted for the proximal humerus. The AO T-plate is a thick plate which cannot be contoured nor bent to fit the proximal humerus bone. It can only be used with large screws. The size of the screw heads may cause impingement under the acromion process.

In addition, while not common, the cloverleaf plate, which is specifically adapted for use in fixating fractures of the tibia and ankle area, has been adapted for fixating the proximal humerus. In order to use the cloverleaf plate for the proximal humerus, a head portion of the cloverleaf plate must be bent and cut to fit the proximal humerus. Frequently, the bending and cutting of the plate creates a stress concentration or worsens an existing stress concentration in the bone plate. These stress concentrations regularly lead to a fatigue failure of the plate when fixed on the proximal humerus for an extended period of time. Moreover, bending and cutting the cloverleaf plate to the proper shape is quite difficult and is not readily accomplished. At best, a rough approximation of the shape of the curvature of the proximal humerus is attempted while the plate still does not adequately cover the greater tuberosity 18 and transition from the proximal humerus shaft 15 to the greater tuberosity 18.

Moreover, in some instances where there are three and four part fractures and a combined fracture and dislocation of the proximal humerus (from the joint space), the common techniques of open reduction and internal fixation are particularly inadequate. In these instances, the conventional response is to replace the fractured bone portion with a prosthetic implant, e.g. artificial proximal humerus, instead of reducing and fixating the fractured area. This approach has been favored in treating four part fractures and fracture dislocations due to the difficulty of managing the reduction with complicated fracture patterns and the difficulty of adapting available plates for fixation in these situations. Nevertheless, because the artificial replacement of a proximal humerus requires significantly more surgery and expense, and since it is preferable to preserve the natural bones whenever possible, it would be desirable to treat these more difficult cases with open reduction and internal fixation with a bone plate.

Moreover, the proximal humerus is not the only location of the body that presents a challenge of open reduction and internal fixation for multiple fractures and/or partial dislocations from a joint space. Specifically, the distal radius area (commonly referred to as the wrist area) is the site of many multiple fractures. However, like the proximal humerus, a lack of available bone plates that are especially adapted to volar (palm side) and especially adapted to dorsal (top side, opposite the palm) hinder regular and successful treatment by fixation of multiple fractures of the distal radius. Both the volar and dorsal aspects of the distal radius have different anatomical structures and therefore commonly require different adaptions when using a single type of conventional plate to treat both locations. Moreover, conventional plates are not conducive to bending by the surgeon without creating a stress concentration or worsening an existing stress concentration in the plate.

Further, in each of these situations (fractures of the proximal humerus, dorsal distal radius, and volar distal radius), the reduction of the fractured bones is done by free hand without a guide or tool or with K-wires to assist in insuring the return of the fractured portions to their proper location. Where a single fracture occurs, the original position of the fractured portion can be easily recognized and the unfractured portion functions as a guide or reference point for reducing and fixating the fractured portion to the unfractured bone portion. However, this challenge is more acute with three and four part fractures, and fracture dislocations since no single portion of the bone remains unfractured. Therefore, no single portion of the fractured bone can act as a stable guide or reference to insure the return of the fractured portions to their proper position and to remain stable to enable proper reduction and fixation of the multiple fractured portions at the same time.

SUMMARY OF THE INVENTION

The bone plate of the present invention is especially adapted to solve the problems pertinent to all fractures of the proximal humerus and more specifically three and four part fractures and fracture dislocations of the proximal humerus. A first bone plate of the present invention is configured and arranged to match the contour of a healthy unfractured proximal humerus. The improved bone plate includes an elongate shaft portion and a head portion. The shaft portion is adapted for receiving bone screws to fix the bone plate to a shaft of a humerus. The head portion includes a first head section and a second head section, with an obtuse angle defined therebetween. The first and second head sections extend laterally away from a longitudinal axis of the shaft portion in generally opposite directions. The first and second head sections are configured and arranged to secure multiple fractures of a head of proximal humerus while preserving the biceps tendon and avoiding impingement against the acromion process. The configuration of the head portion permits the bone plate to be used immediately without having to cut portions of the head portion as is typically the case with conventional cloverleaf and AO-T plates. Moreover, the plate of the present invention can be used as a guide in reducing the fracture prior to fixation since the plate has a precontoured shape matching the shape of an unfractured proximal humerus.

A bone plate of the present invention also includes a bone plate especially adapted for fixing fractures of the distal radius on the dorsa side as well as a bone plate especially adapted for fixing fractures of the distal radius on the volar (or palmar side). In either case, the bone plate is pre-shaped to match the contour of the anatomic shape of an unfractured distal radius to assist in reduction of complicated fractures and to avoid bending and cutting of a conventional plate, which can result in a fatigue failure and fracture of the plate.

BRIEF DESCRIPTION OF THE DRAWINGS

FIG. 4 is a cross-sectional view of the bone plate of FIG. 2 as taken along lines 4—4 of FIG. 2.

FIG. 5 is a cross-sectional view of the bone plate FIG. 2 as taken along lines 5—5 of FIG. 2.

FIG. 5B is a cross sectional view of FIG. 2 taken along lines 5B—5B.

FIG. 6 is an enlarged perspective view of the bone plate of the present invention mounted to a proximal humerus.

FIG. 7 is a cross-sectional view of FIG. 6 taken along lines 7—7.

FIG. 10 is a top plan view of the bone plate of the present invention for the dorsal side of the distal radius of the left forearm.

FIG. 11 is a cross-sectional view of the bone plate of the present invention taken along line 11—11 of FIG. 10.

FIG. 12 is a cross-sectional view of the bone plate of the present invention taken along line 12—12 of FIG. 10.

FIG. 13 is a top plan view of the bone plate of the present invention for the dorsal side of the distal radius of the right forearm.

FIG. 14 is a cross-sectional view of the bone plate of the present invention taken along line 14—14 of FIG. 13.

FIG. 15 is a cross-sectional view of the bone plate of the present invention taken along line 15—15 of FIG. 13.

FIG. 16 is a top plan view of the bone plate of the present invention for the volar side of the distal radius of the left forearm.

FIG. 17 is a cross-sectional view of the bone plate of the present invention taken along line 17—17 of FIG. 16.

FIG. 18 is a perspective view of the bone plate of the present invention for the volar side of the distal radius of the left forearm.

FIG. 18A is a cross sectional view of FIG. 16 taken along lines 18A—18A.

FIG. 19 is a top plan view of the bone plate of the present invention for the volar side of the distal radius of the right forearm.

FIG. 20 is a cross-sectional view of the bone plate of the present invention taken along line 20—20 of FIG. 19.

FIG. 21 is a perspective view of the bone plate of the present invention for the volar side of the distal radius of the right forearm.

DETAILED DESCRIPTION OF THE PREFERRED EMBODIMENTS

Figure 1:
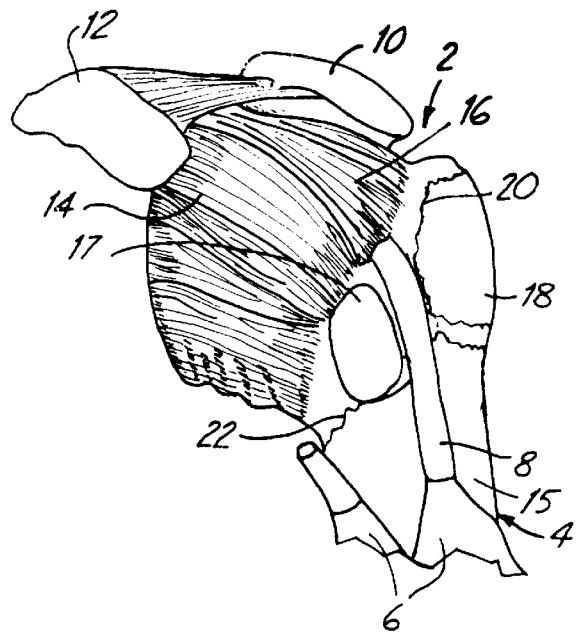
FIG. 1 is plan view of a left shoulder joint as seen from an anterior orientation.

FIG. 1 shows an anterior view of the left shoulder joint. The shoulder joint 2 generally includes: proximal humerus 4, biceps muscle 6, biceps tendon 8, acromion process 10, coracoid process 12, and articular capsule 14. Proximal humerus 4 includes shaft 15, head 16, including lesser tuberosity 17 and greater tuberosity 18. Fractures of the proximal humerus typically separate the humerus head 16 from the humerus shaft 15, and at times also separates the greater tuberosity 18 and the lesser tuberosity 17 from head 16. These fractures are depicted, in part, by vertical fracture line 20 extending about the greater tuberosity 18 and by horizontal fracture line 22 extending across the humerus shaft 15. A bone plate 30 of the present invention as shown in FIGS. 2–9 is adapted for reduction and internal fixation of all fractures of the proximal humerus and especially adapted for reduction and internal fixation of three and four part fractures of proximal humerus 4.

Figure 2:
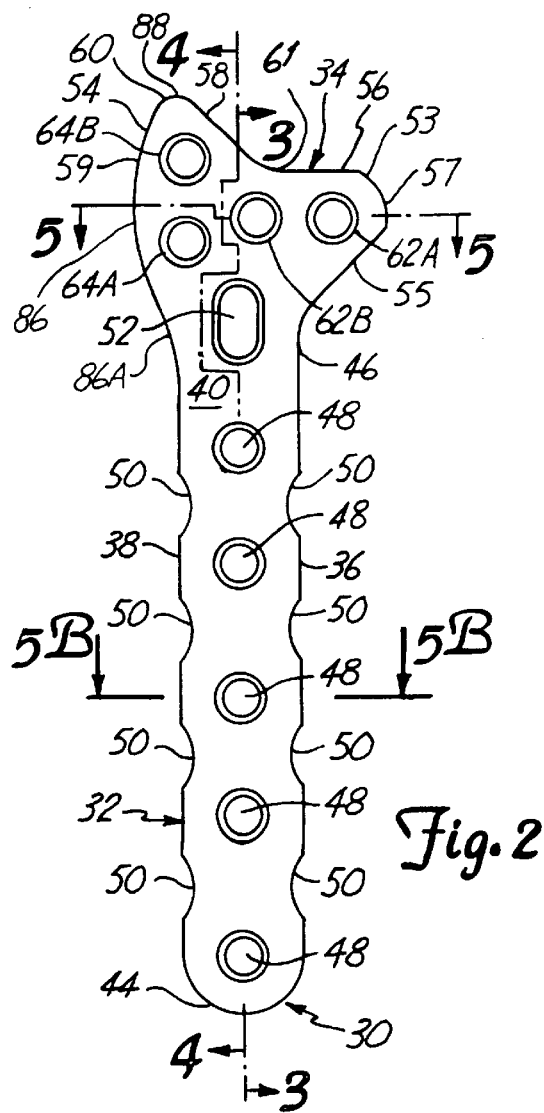
FIG. 2 is a top plan view of a bone plate of the present invention for the proximal humerus of the left arm.

A bone plate of the present invention for internally fixating fractures in the proximal humerus is illustrated generally in FIG. 2 at 30. Bone plate 30 includes elongate shaft portion 32 and head portion 34. As shown in FIG. 2, elongate shaft portion 32 is a generally elongate member having first side 36, second side 38, outer surface 40, inner surface 42, distal end 44 and proximal end 46. Elongate shaft portion 32 has a plurality of holes 48 and has a plurality of curved notches 50 located along the edges of first side 36 and second side 38. Proximal end 46 of elongate shaft portion 32 includes an elongate hole 52. The holes 48 and hole 52 are aligned along a central longitudinal axis of the shaft portion 32.

Head portion 34 extends from proximal end 46 of elongate shaft portion 32 and includes first head section 53 and second head section 54. First head section 53 includes first side 55, second side 56, and tip 57 while second head section 54 includes an extension portion 88 and a lateral portion 86 with the extension portion 88 having a first side 58, a second side 59, and a tip 60. Lateral portion 86 has a radius of curvature of about 1.0 and the transition portion 86A distal to the lateral portion 86 has a radius of curvature of about 1.0. Tip 57 has a radius of curvature of about 0.240 while tip 60 has a radius of curvature of about 0.10. First head section 53 also includes a pair of holes 62A and 62B and second head section 54 also includes a pair of holes 64A and 64B.

First head section 53 of head portion 34 has a generally trapezoidal shape and extends laterally away from and generally perpendicular to a longitudinal axis of shaft portion 32. Moreover, the second side 56 of first section 53 is generally perpendicular to a longitudinal axis of elongate shaft section 32. Preferably, first side 55 of first head section 53 and first side 36 of elongate shaft portion 32 form an obtuse angle of about 135 degrees. Tip 57 has a generally arcuate shape.

Second head section 54 of head portion 34 has a generally curved shape and extends laterally away from second side 38 of elongate shaft portion 32 and in a generally opposite direction from first head section 53. First side 58 of extension portion 88 of second head portion 54 and second side 56 of first head section 53 form an obtuse angle of 135 degrees. Gap 61 is defined between second side 56 of first head section 53 and first side 58 of second head section 54 and is configured and arranged to avoid impinging on acromion process 10 once plate 30 is fixed to proximal humerus 4.

Extension portion 88 of second head section 54 extends along a line generally perpendicular to but spaced from a central longitudinal axis of elongate shaft section 32. Tip 60 of extension portion 88 points in a direction generally opposite from elongate shaft section 32.

Holes 62A, 62B of first head section 53 are aligned along a common axis which is generally perpendicular to a central longitudinal axis of elongate shaft portion 32. Holes 64A, 64B of second head section 54 are located along a common axis which is generally parallel to a central longitudinal axis of elongate shaft portion 32 and preferably located between a central longitudinal axis of elongate shaft portion 32 and second side 38 of elongate shaft portion 32. Hole 64A of second head section 54 is preferably located closer to proximal end 46 of elongate shaft portion 32 than holes 62A, 62B of first head section 53.

Holes 62A, 62B of first head section 53 are located so that a common central axis of holes 62A, 62B extends generally between the hole 64A and hole 64B of second head section 54. This configuration results in holes 62A, 62B and holes 64A, 64B of head portion 34 having a generally T-shaped configuration in which holes 62A, 62B of first head section 53 form the shaft of the "T" configuration and holes 64A, 64B of second head section 54 form the cross-bar of the "T" configuration.

As shown on FIG. 2, holes 48 and 52 of shaft portion 32 and holes 62A,62B and 64A, 64B of head portion 34 extend through bone plate 30 and preferably are counter-sunk for receiving bone screws and minimizing screw protrusion above bone plate 30. Holes 62A, 62B and 64A, 64B of head portion 34 are adapted for receiving and supporting cancellous bone screws (not shown) while holes 48 and 52 are adapted for receiving and supporting cortical bone screws (not shown).

Figure 3:
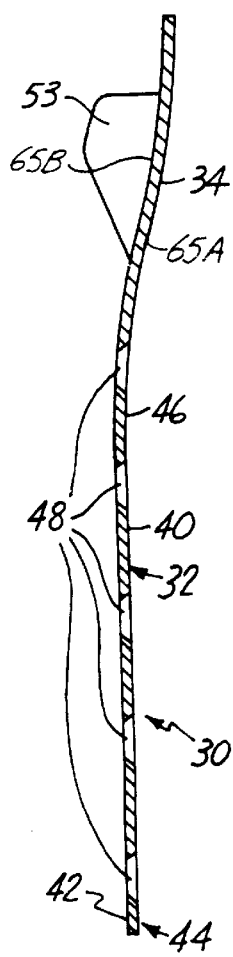
FIG. 3 is a cross-sectional view of the bone plate of FIG. 2 as taken along lines 3—3 of FIG. 2.

FIGS. 3 and 4 are sectional views of bone plate 30. As shown in FIG. 3, head portion 34 and proximal end 46 of elongate shaft portion 32 form a generally obtuse angle of about 170 degrees relative to the plane of a majority of elongate shaft portion 32 with upper transition surface 65A having a radius of curvature of 4.0, and inner surface 65B having a longitudinal radius of curvature of 3.25. As a result, head portion 34 is raised relative to elongate shaft portion 32 which results in better conformity with the shape of greater tuberosity 18 of the proximal humerus 4 (shown in FIGS. 6–8).

As best shown in FIG. 5, head portion 34 preferably has a concave inner surface 66 for abutting the surface of the humerus and has a transverse radius of curvature of about 0.875. As shown in FIG. 5B, inner surface 42 of elongate shaft portion 32 is preferably contoured so as to abut and conform with the curved surface of the humerus and has a radius of curvature of about 0.875. Preferably, inner surface 42 is concave along a line parallel to a length of elongate shaft portion 32. Thus, bone plate 30, including elongate shaft portion 32 and head portion 34, is "anatomically" shaped to conform to the curvature of a healthy unfractured proximal humerus. As a result, elongate shaft portion 32 better stabilizes head portion 34 of the bone plate 30 for more secure positioning of bone plate 30 against the humerus and for more secure positioning of bone screws in the fractured bone (shown in FIGS. 6–8). Significantly, this shape makes it unnecessary to prebend the shape of the plate prior to fixing the plate on the humerus.

In one embodiment of the present invention, the overall length of bone plate 30 is about 4 inches and the thickness of bone plate 30 is about 0.050 inches. The overall length of bone plate 30 is a combination of the length of elongate shaft portion 32 (about 2.3 inches) and the length of head section 34. The width of elongate shaft portion 32 is about 0.550 inches. The maximum width of head portion 34 is about 1.1 inches.

Bone plate 30 is preferably formed from titanium alloy (Ti-6Al-4V). This titanium alloy is about 90 percent stronger in fatigue than bone plates made with AISI Type 316L stainless steel, and about 50 percent stronger than "commercially pure" titanium (grade 4). Thus, forming bone plate 30 from this material causes bone plate 30 to be superior against fatigue.

Figure 8:
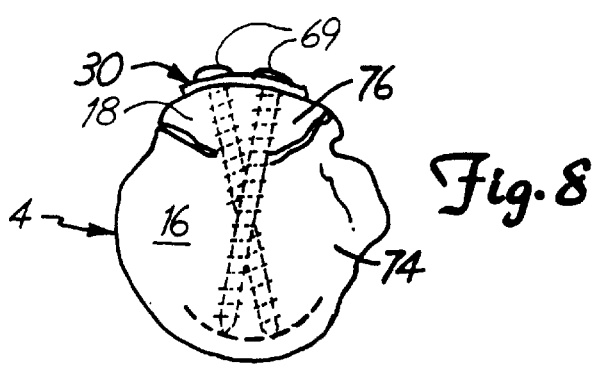
FIG. 8 is a cross-sectional view of the bone plate of FIG. 6 taken along lines 8—8.

In use, bone plate 30 is mounted to proximal end 72 of humerus 4 which contains shaft 15 and humeral head 16. FIG. 6 illustrates humerus 4 having a bone plate 30 of present invention affixed across various fracture sites (e.g. fracture lines 20 and 22). FIG. 7 is a cross-sectional view of bone plate 30 of FIG. 6 (as taken along lines 7—7) attached and mounted to proximal end 72 of humerus 2 by cancellous bone screws 69 and cortical bone screws 68. FIG. 8 is a cross-sectional view of bone plate 30 of FIG. 6 (as taken along lines 8—8) attached and mounted to humerus 2 by cancellous bone screws 69.

As best shown in FIG. 7, humerus 4 includes a vertical fracture line 20 and horizontal fracture line 22 so as to form main bone fragments 74 (head 16) and 75 (shaft 15) and a smaller bone fragment 76 (separating greater tuberosity 18). Cancellous bone screws 69 and cortical bone screws 68 are used, as known in the art, in conjunction with bone plate 30 to reduce and fixate bone fragments 74, 75 and 76 together.

The method of repairing the proximal humerus having multiple fractured portions includes reducing the fractured portions to their original position, aligning the bone plate 30 so that lateral portion 86 of second head portion 54 is adjacent and posterior to biceps tendon 8 and so that superior tip 60 of extension portion 88 of the plate 30 rests adjacent the superior tip of the greater tuberosity 18. When fixed in this position, the biceps tendon 8 is preserved and remains in its natural location between lesser tuberosity 17 and greater tuberosity 18 and the tip 60 and gap 61 of plate head portion 34 will avoid impinging the acromion process 10 (when the proximal humerus 4 is rotated upward toward the acromion process during normal use of the arm after surgery). After positioning the plate 30, cancellous screws 69 are then inserted into holes 62A,62B, 64A, 64B of head portion 34 and cortical screws 68 are inserted into holes 48 of elongate shaft portion to fix the plate 30 to the head 16 and shaft 15 of the proximal humerus 4. Conventionally known thin K-wires can be used to temporarily fixate the bone fragments after reduction and prior to fixation with the bone plate.

When complicated multiple fractures occur, the bone plate 30 is used as a guide for reducing the fractured bone portions into their original position since the curvature of the head portion 34 of the bone plate 30 matches the natural shape and contour of a head of an unfractured proximal humerus. In even more complicated situations, the bone plate 30 may first be fixed to the shaft 15 of the proximal humerus 4 and the plate head portion 34 (and transition from head portion 34 to shaft portion 32) is then used as a guide to reduce the multiple fractured portions. This precontoured shape of the bone plate 30 is very significant since it requires no bending (or very little) to match the shape of the proximal humerus and since it permits the plate to act as a guide during reduction of the fractures. A conventional cloverleaf plate does not carry this precontoured shape of the proximal humerus. It would also be quite difficult to bend the cloverleaf plate to the proper shape of the proximal humerus in a multiple fracture situation since the proximal humerus to be repaired would lack the proper unfractured shape to act as a guide to shape and bend the cloverleaf bone plate. Moreover, the amount of bending and the number of rough edges produced by cutting to re-configure the cloverleaf plate greatly increases the chance of fatigue failure. These rough edges of the conventional cloverleaf plate can also pose additional risk of injury to tissues adjacent the proximal humerus. However, the bone plate 30 of the present invention includes smooth edges such as lateral portion 86 so that any tissue injury associated with the edges of the bone plate 30 are unlikely.

Finally, the extension portion 88 of the second head portion 54 enables insertion of a cancellous screw in a location higher on the greater tuberosity 18 than possible with conventional plates since the superior portion of a conventional cloverleaf plate must be removed in order to permit placement on the proximal humerus and avoidance of the acromion process 10. This arrangement permits greater flexibility in placing screws and insures proper fixation of bone plate 30 on and through greater tuberosity 18 to proximal humerus head 16.

Figure 9:
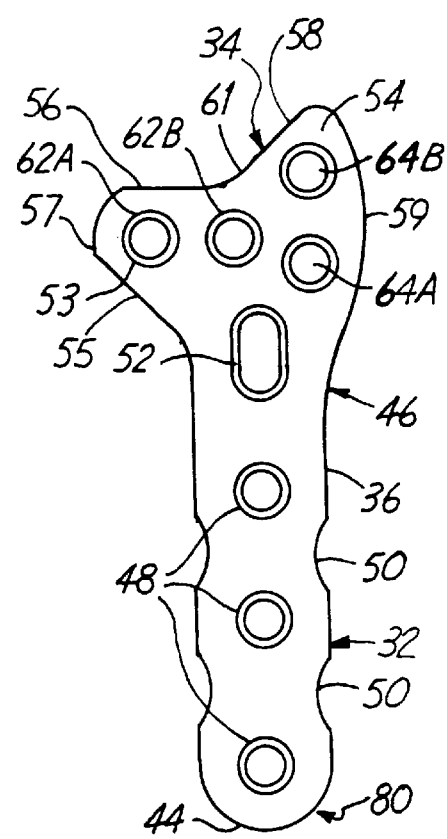
FIG. 9 is a top plan view of a bone plate of the present invention for the proximal humerus of the right arm.

FIG. 9 illustrates a bone plate 80 which is an alternate embodiment of bone plate 30 shown in FIGS. 2–8. For ease of illustration, those elements of bone plate 80 which are the same as those elements of bone plate 30 are numbered similarly. Bone plate 80 has similar features to bone plate 30 except that the overall length is shorter due to elongate shaft portion 32 being shorter. This results in elongate shaft portion 32 of bone plate 80 containing only three holes 48, whereas elongate shaft portion 32 of bone plate 30 defines five circular holes 48. Bone plate 80 also has an opposite orientation than bone plate 30 in order to fixate fractures of the proximal humerus of the opposite arm. In all other respects, bone plate 80 is identical to bone plate 30.

A bone plate of the present invention for fixating fractures of the dorsal distal radius is illustrated in FIG. 10 at 90. The dorsal plate is indicated for use in all unstable fractures of the distal radius with posterior dislocation. It is frequently indicated in fractures where the articular surface is partially involved. In complex fractures where depressed areas in the articular surface cannot be reduced by traction, open reduction and plating are mandatory. It is also indicated in extension-type fractures with secondary displacement.

Bone plate 90 generally includes an elongate shaft portion 92 and head portion 94. As best shown in FIG. 10, elongate shaft portion 92 is a generally elongate member having first side 96, second side 98, outer surface 100, inner surface 102, distal end 104 and proximal end 106. Elongate shaft portion 92 defines a plurality of circular holes 108 and an elongate hole 110. Elongate shaft portion 92 also has a plurality of curved notches 112 located along the edges of first side 96 and second side 98.

Head portion 94 extends from distal end 104 of elongate shaft portion 92 and defines a plurality of circular holes 122.

Holes 108 and 110 are centered along a central longitudinal axis of elongate shaft portion 92. One circular hole 108 is located adjacent to the proximal side of elongate hole 110, while the other circular hole 108 is located adjacent to the distal side of elongate hole 110.

FIG. 11 illustrates that head portion 94 preferably extends at a mild angle with respect to the plane of elongate shaft portion 92. As a result, head portion 94 is shaped conformity with the shape of the distal radius (shown in FIG. 22), particularly the styloid process at the distal end of the radius. Head portion 94 extends from distal end 104 of elongate shaft portion 92 and is shaped to define a longitudinal curved outer surface 115A having a radius of curvature of 6.25 and a curved inner surface 115B having a transverse radius of curvature of 1.5. Curved inner surface 115B is adapted to follow the contour of the distal end of the distal radius bone on the dorsal side.

As seen in FIG. 10, preferably, head portion 94 extends from first side 96 of elongate shaft portion 92 to define a first transition portion 117A having a radius of curvature of 1.25 while a second transition portion 117B has a radius of curvature of 0.75. Head portion 94 extends from second side 98 of elongate shaft portion 92 to define a transition portion 119A having a radius of curvature of about 1.25. First corner section 114 and second corner section 116 of head section 94 extend away from the axial center of elongate shaft portion 92 in generally opposite directions and are generally rounded, creating a smooth profile. First corner section 114 is more sharply curved (having a radius of curvature of about 0.088) and extends further distally from distal end 104 of elongate shaft portion 92 than second corner section 116 (having a radius of curvature of about 0.188). The distal end 120 of head portion 94 is slightly concave and defines a third transition portion 117C between first corner section 114 and second corner section 166 with the transition portion 117C having a radius of curvature of about 1.7. Head portion 94 defines a plurality of circular holes 122 for receiving bone screws for maximizing fixation of multiple bone fragments at the distal end of the radius.

Holes 122 of head portion 94 are generally oriented to form the outline of a triangle. The grouping of circular holes 122 furthest from the shaft portion consists of three holes aligned in a slightly concave column. The next grouping of holes 122 closest to the shaft portion contains two circular holes 122. The grouping of circular holes 122 in head portion 94 immediately adjacent the shaft portion 92 is a single hole located near the distal end 104 of elongate shaft portion 92. Taken as a group, circular holes 122 of head portion 94 form a general outline of a triangle.

Circular holes 122 of head portion 94 and circular holes 108 and elongate hole 110 of elongate shaft portion 92 extend through bone plate 90 and preferably are countersunk for receiving bone screws and minimizing screw protrusion above bone plate 90. Because head portion 94 provides a plurality of locations for receiving bone screws, multiple smaller bone fractures may be fixed by these bone screws and more fixation screws can be used at the utmost distal portion of the distal radius.

As best shown in FIG. 12, a fourth transition portion of head portion 94 (extending from elongate shaft portion 92) preferably has a concave inner surface 124 for abutting the surface of the distal radius and defines a radius of curvature of about 0.625. Inner surface 102 of elongate shaft portion 92, extends proximally from inner surface 124, is preferably contoured so as to abut and conform with the curved surface of the shaft of the distal radius (shown in FIG. 22) and has a milder radius of curvature of about 1.0. Preferably, inner surface 102 is concave along a line parallel to a length of elongate shaft portion 92. Thus, bone plate 90, including elongate shaft portion 92 and head portion 94, is "anatomically" shaped to conform to the general shape of a healthy unfractured distal radius. As a result, elongate shaft portion 92 better stabilizes head portion 94 of bone plate 90 for more secure positioning of bone plate 90 against the distal radius and for more secure positioning of bone screws in the fractured bone (shown in FIG. 22). Specifically, head portion 94 defines a shaped surface adapted with an anatomical precontoured shape to match the surface of the styloid process of the distal radius. For example, first corner section 114 is arranged to provide support for the styloid process and permit fixation of a screw in distally remote location not possible with conventional plates. This overall arrangement permits the plate to placed more distally on the distal radius than conventional plates and permits an additional cluster of fixation screw holes to be available at the utmost distal portions of the distal radius for better fixation. Conventional plates lack an appropriate shape and curvature to permit the utmost distal placement of the plate and lack an additional cluster of fixation screw holes.

The low profile of the plate and its anatomical shape allow for distal placement on the radius and its use as a buttress plate. The numerous screw holes allow for fixation of comminuted fractures with multiple fragments although not all screws need to be inserted.

In one form of the present invention, the overall length of bone plate 90 is about 2.190 inches. The thickness of elongate shaft portion is about 0.050 inches, while the thickness of head portion 94 varies from of the order of between of 0.050 inches closest to the shaft to about 0.030 inches at a point furthest from the shaft. The width of elongate shaft portion 92 is about 0.40 inches, with the notched sections 112 of elongate shaft portion 92 having a slightly lesser width. The maximum width of head portion 94 is about 0.970 inches.

Bone plate 90 is preferably formed from titanium alloy (Ti-6Al-4V). This titanium alloy is about 90 percent stronger in fatigue than bone plates made with AISI Type 316L stainless steel, and about 50 percent stronger than "commercially pure" titanium (grade 4). Thus, forming bone plate 90 from this material causes bone plate 90 to be superior against fatigue.

FIG. 13 illustrates a bone plate 130 of the present invention which is similar to the bone plate 90 shown in FIGS. 10–12. For ease of illustration, those elements of bone plate 130 which are the same as those elements of bone plate 90 are numbered similarly. Bone plate 130 has similar features to bone plate 90 except that its width is narrower to better conform to narrower bones. As shown, bone plate 130 has an opposite orientation than bone plate 90 in order to fixate fractures of the distal radius of the opposite arm. In all other respects, bone plate 130 is identical to bone plate 90 with small variations in the radii of curvature relative to plate 90 as detailed below. For example, first transition portion 117A has a radius of curvature of 1.25, second transition portion 117B has a radius of curvature of about 0.5 and transition portion 117C has a radius of curvature of about 0.625. First corner section 114 has a radius of curvature of about 0.159 and second corner section 116 has a radius of curvature of about 0.125. Finally, inner surface 124 (FIG. 15) of head portion 94 has a radius of curvature of about 0.75 which extends proximally to the inner surface of the elongate shaft portion which has a radius of about 0.625.

FIG. 14 illustrates that head portion 92 preferably extends at an angle with respect to the plane of elongate shaft portion 92 of bone plate 130. Thus, head portion 94 is shaped in conformity with the shape of the distal radius (shown in FIG. 22). As best shown in FIG. 15, head portion 94 preferably has a contoured inner surface 124 for abutting the surface of the distal radius that has a radius of curvature of about 0.75. As previously discussed, the "anatomical" shape of bone plate 130 increases stability of bone plate 130, particularly as the shape of the bone matches of the shape of the styloid process, and allows for more secure positioning of bone screws in the fractured bone (shown in FIG. 22).

A bone plate of the present invention for fixating fractures of the volar distal radius is illustrated in FIG. 16 at 140. The volar plate is indicated in all unstable fractures of the distal radius with anterior dislocation. The classical indicator is the reversed Barton fracture with a small palmar fragment. As for the dorsal plate, the volar plate is also indicated in severely comminuted fractures of the distal radius where depressed areas of the articular surface cannot be reduced by traction. Often times, a double approach using both dorsal and volar plates is necessary to reduce the fracture.

Bone plate 140 generally includes an elongate shaft portion 142 coupled to head portion 144. As best shown in FIGS. 16 and 17, elongate shaft portion 142 is a generally elongate member having first side 146, second side 148, inner surface 150, outer surface 152, distal end 154 and proximal end 156. Elongate shaft portion 142 defines a plurality of circular holes 158 and an elongate hole 160. Elongate shaft portion 142 also has a plurality of curved notches 162 located along the edges of first side 146 and second side 148.

Head portion 144 extends from proximal end 156 of elongate shaft portion 142. Head portion 144 is somewhat in the shape of a curved trapezoid, and defines a plurality of circular holes 172.

Holes 158 and hole 160 are all centered along a central longitudinal axis of elongate shaft portion 142. One circular hole 158 is located adjacent the proximal side of elongate hole 160, while the other circular hole 158 is located adjacent the distal side of elongate hole 160. FIG. 17 illustrates that head portion 144 preferably extends at an angle of about 160 degrees with respect to the plane of elongate shaft portion 142. As a result, head portion 144 is raised with respect to elongate shaft portion 142 which results in better conformity with the shape of the utmost distal portion of the distal radius on the volar side.

Head portion 144 integrally extends from distal end 154 of elongate shaft portion 142. Preferably head portion 144 extends from first side 146 of elongate shaft portion 142 to define a radius of curvature of about 1.25. Head portion 144 extends from second side 148 of elongate shaft portion 142 to define a radius of curvature of about 1.25. First corner section 164 and second corner section 166 of head section 144 extend away from the axial center of elongate shaft portion 142 in generally opposite directions and are generally rounded, creating a smooth profile. First corner section 164 is more sharply curved (having a radius of curvature of about 0.188) and extends further distally from distal end 154 of elongate shaft portion 142 than second corner section 166 (having a radius of curvature of about 0.225). The distal end 170 of head portion 144 is slightly concave and has a radius of curvature of about 1.7. Head portion 144 defines a plurality of circular holes 172 for receiving bone screws.

Circular holes 172 of head portion 1494 are generally oriented to form the outline of a triangle. The most distal grouping of circular holes 172 consists of three such holes aligned in a slightly concave column. The next most distal grouping contains two circular holes 172. The most proximal grouping of circular holes 172 in head portion 144 is a single hole located near the distal end 154 of elongate shaft 142. Taken as a group, circular holes 172 of head portion 144 form a general outline of a triangle.

Circular holes 172 of head portion 144 and circular holes 158 and elongate hole 160 of elongate shaft portion 142 extend through bone plate 140 and preferably are countersunk for receiving bone screwing and minimizing screw protrusion above bone plate 140. Because head portion 144 provides a plurality of locations for receiving bone screws, multiple smaller bone fractures may be fixed by these bone screws and more fixation screws can be used at the utmost distal portion of the distal radius.

As best shown in FIG. 18, head portion 144 preferably has a contoured surface 174 for abutting the surface of the distal radius. Inner surface 152 of elongate shaft portion 142 is preferably contoured so as to abut and conform with the curved surface of the distal radius. Preferably, inner surface 150 of shaft portion 142 is concave along a line parallel to a length of elongate shaft portion 142. Thus, bone plate 140, including elongate shaft portion 142 and head portion 144, is "anatomically" shaped to conform to the general shape of a healthy unfractured distal radius. As a result, elongate shaft portion 142 better stabilizes head portion 144 of bone plate 140 for more secure positioning of bone plate 140 against the distal radius and for more secure positioning of bone screws in the fractured bone. Specifically, head portion 144 defines a shaped surface adapted with an anatomical precontoured shaped to match the surface of the styloid process of the distal radius and can be used as a guide for reduction of complex fractures.

FIG. 18A illustrates a cross section of bone plate 140 of FIG. 16 as taken along lines 18A—18A. FIG. 18A shows corner section 166 forming a generally obtuse angle of about 150 degrees relative to the remainder of head portion 144 (with the curvature between corner section 166 and the remainder of head portion 144 having a radius of curvature of about 0.5) to insure conformity with the utmost distal (and lateral) portions of the distal radius on the volar side.

In one embodiment, the overall length of bone plate 140 is about 2.080 inches. The thickness of elongate shaft portion 124 is about 0.050 inches, while the thickness of head portion 144 varies from about 0.050 inches at a proximal end closest to the shaft portion to about 0.030 inches at distal end 170. The width of elongate shaft portion 142 is about 0.40 inches, with the notched sections 162 of elongate shaft portion 142 having a slightly lesser width. The maximum width of head portion 144 is about 0.950 inches.

Bone plate 140 is preferably formed from titanium alloy (Ti-6Al-4V). This titanium alloy is about 90 percent stronger in fatigue than bone plates made with AISI Type 316L stainless steel, and about 50 percent stronger than "commercially pure" titanium (grade 4). Thus, forming bone plate 140 from this material causes bone plate 140 to be superior against fatigue.

FIG. 19 illustrates a bone plate 180 similar to bone plate 140 shown in FIGS. 16–18. For ease of illustration, those elements of bone plate 180 which are the same as those elements of bone plate 140 are numbered similarly. Bone plate 180 has similar features to bone plate 140 except that its width is narrower to better conform to narrower bones. Bone plate 180 has an opposite orientation than bone plate 140 in order to fixate fractures of the distal radius of the opposite arm (e.g. right arm). Finally, bone plate 180 includes a flange 182 to facilitate matching the curvature of the distal radius. In all other respects, bone plate 180 is identical to bone plate 140.

FIG. 20 illustrates that head portion 144 preferably extends at an angle of about 160 degrees with respect to the plane of elongate shaft portion 142 of bone plate 180. Thus, head portion 144 is raised with respect to elongate shaft portion 142 of bone plate 180 which results in better conformity with the shape of the distal radius. As shown in FIG. 20, flange 182 forms a generally obtuse angle relative to the head portion 144 of approximately 150 degrees with angle being on a generally opposite surface of plate 180 than the obtuse angle formed between head portion 144 and elongate shaft portion 142. As best shown in FIG. 21, head portion 144 preferably has a contoured surface 174 for abutting the surface of the distal radius and includes flange 182.

In comminuted fractures or fractures associated with a break of the styloid process of the radius, the lip or flange 182 of the longer volar plate, gives more support in maintaining the reduction of the styloid process. An extra screw may be inserted through the plate to fix the styloid process whenever the size of the fragment is amenable to screw fixation. This often avoids the use of lag screws in already shattered bone.

As previously discussed, the "anatomical" shape of bone plate 180 increases stability of bone plate 180 and allows for more secure positioning of bone screws in the fractured bone.

Figure 22:
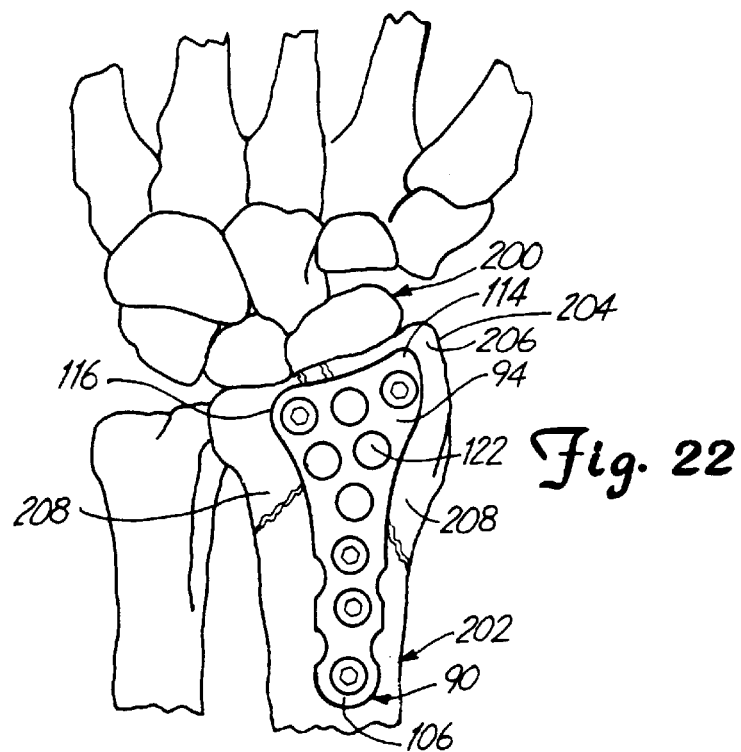
FIG. 22 is a perspective view of the bone plate of the present invention mounted to the dorsal side of the distal radius.

FIG. 22 illustrates internal fixating bone plate 90 of present invention implanted and mounted to a dorsal side of a distal radius. FIG. 22 illustrates a wrist 200 and distal radius 202, which includes a distal end 204, styloid process 206 and fracture fragments 208. Plate 90 (see FIG. 10) is fixed to radius 202 by screws known to those skilled in the art placed in holes 122 and 108 as necessary to fix bone plate 90 to fracture fragments 208 after their reduction. Of course, in cases with complicated multiple fractures, bone plate 90 can be used as a guide to reduce the bone fragments 208 into the proper position since bone plate 90 is precontoured to match the shape of an unfractured dorsal side of a distal radius.

Figure 23:
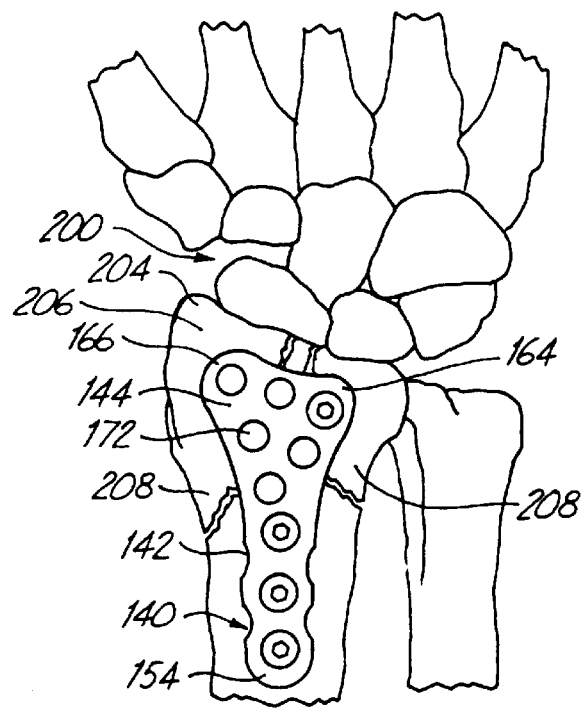
FIG. 23 is a perspective view of the bone plate of the present invention mounted to the volar side of the distal radius.

FIG. 23 illustrates internal fixating bone plate 140 of present invention implanted and mounted to volar side of a distal radius. FIG. 23 illustrates a wrist 200 and distal radius 202, which includes a distal end 204, styloid process 206 and fracture fragments 208. Plate 90 (see FIG. 16) is fixed to radius 202 by screws known to those skilled in the art placed in holes 122 and 108 as necessary to fix bone plate 90 to fracture fragments 208 after their reduction. Of course, in cases with complicated multiple fractures, bone plate 90 can be used as a guide to reduce the bone fragments 208 into the proper position since bone plate 90 is precontoured to match the shape of an unfractured volar side of a distal radius.

Although the present invention has been described with reference to preferred embodiments, workers skilled in the art will recognize that changes may be made in form and detail without departing from the spirit and scope of the invention.

What is claimed is:

1. A bone plate for fixing proximal humerus fractures comprising:

an elongate shaft portion with at least one hole extending through the shaft portion for securing the plate to a shaft of the proximal humerus; and a head portion extending from the elongate shaft portion, including:

a first portion extending laterally outward from and generally perpendicular to a longitudinal axis of the elongate shaft portion; and a second portion which extends laterally outward from a longitudinal axis of the elongate shaft portion in a generally opposite direction than the first head portion and includes an extension portion extending in a direction generally opposite the elongate shaft section, wherein the extension portion of the second head portion extends along a line generally parallel to but spaced from the central longitudinal axis of the elongate shaft portion, wherein the head portion has a transverse cross sectional curvature substantially matching the curvature of an anatomic shape of an unfractured lateral proximal humerus and a longitudinal cross sectional curvature substantially matching the curvature of the greater tuberosity of the proximal humerus.

2. The bone plate of claim 1 wherein a first edge of the first head portion extends generally perpendicular to a longitudinal axis of the elongate shaft portion with the first edge of the first head portion and a first edge of the extension head portion forming an obtuse angle configured and arranged to avoid impingement with an acromion process of the shoulder.

3. The bone plate of claim 2 wherein the extension portion extends beyond the first edge of the first head portion in a direction generally opposite the elongate shaft portion.

4. The bone plate of claim 3 wherein the obtuse angle is about 135 degrees.

5. The bone plate of claim 1 wherein the first head portion includes a plurality of holes extending there through for receiving bone screws wherein the holes are aligned along a longitudinal axis generally perpendicular to a central longitudinal axis of the elongate shaft portion.

6. A bone plate for fixing proximal humerus fractures comprising:

an elongate shaft portion with at least one hole extending through the shaft portion for securing the plate to a shaft of the proximal humerus; and a head portion extending from the elongate shaft portion, including:

a first portion extending laterally outward from and generally perpendicular to a longitudinal axis of the elongate shaft portion; and a second portion which extends laterally outward from a longitudinal axis of the elongate shaft portion in a generally opposite direction than the first head portion and includes an extension portion extending in a direction generally opposite the elongate shaft section, wherein the extension portion of the second head portion extends along a line generally parallel to but spaced from the central longitudinal axis of the elongate shaft portion, wherein a second edge of the first portion of the head portion and a first side of the elongate shaft portion form an obtuse angle of about 135 degrees.

7. A bone plate for fixing proximal humerus fractures comprising:

an elongate shaft portion with at least one hole extending through the shaft portion for securing the plate to a shaft of the proximal humerus; and a head portion extending from the elongate shaft portion, including:

a first portion extending laterally outward from and generally perpendicular to a longitudinal axis of the elongate shaft portion; and a second portion which extends laterally outward from a longitudinal axis of the elongate shaft portion in a generally opposite direction than the first head portion and includes an extension portion extending in a direction generally opposite the elongate shaft section, wherein the extension portion of the second head portion extends along a line generally parallel to but spaced from the central longitudinal axis of the elongate shaft portion, wherein a majority of the head portion extends in a plane that forms a generally obtuse angle relative to a plane of the elongate shaft portion.

8. A bone plate for fixing proximal humerus fractures comprising:

an elongate shaft portion with at least one hole extending through the shaft portion for securing the plate to a shaft of the proximal humerus; and a head portion extending from the elongate shaft portion, including:

a first portion extending laterally outward from and generally perpendicular to a longitudinal axis of the elongate shaft portion; and a second portion which extends laterally outward from a longitudinal axis of the elongate shaft portion in a generally opposite direction than the first head portion and includes an extension portion extending in a direction generally opposite the elongate shaft section, wherein the extension portion of the second head portion extends along a line generally parallel to but spaced from the central longitudinal axis of the elongate shaft portion, wherein an outer edge of the second portion of the head portion is oblique to the elongate shaft portion and forms a smooth curved edge, wherein the outer edge joins a first edge of the extension portion to define a vertex of the extension portion of the second head portion, the vertex pointing in a direction generally opposite the elongate shaft portion.

9. A bone plate for fixing proximal humerus fractures comprising:

an elongate shaft portion with at least one hole extending through the shaft portion for securing the plate to a shaft of the proximal humerus; and a head portion extending from the elongate shaft portion, including:

a first portion extending laterally outward from and generally perpendicular to a longitudinal axis of the elongate shaft portion; and a second portion which extends laterally outward from a longitudinal axis of the elongate shaft portion in a generally opposite direction than the first head portion and includes an extension portion extending in a direction generally opposite the elongate shaft section, wherein the extension portion of the second head portion extends along a line generally parallel to but spaced from the central longitudinal axis of the elongate shaft portion, wherein the second head portion includes a plurality of holes extending there through for receiving bone screws wherein the holes are aligned along a longitudinal axis generally parallel to but spaced from a central longitudinal axis of the elongate shaft portion.

10. A bone plate for fixing fractures of a volar aspect of a distal radius, the plate comprising:

an elongate shaft portion with at least one hole extending through the shaft portion for securing the plate to a shaft of the distal radius; and a head portion extending from the elongate shaft portion, including:
- a first portion extending laterally outward from and generally perpendicular to a longitudinal axis of the elongate shaft portion; and
- a second portion extending laterally outward from and generally perpendicular to a longitudinal axis of the elongate shaft portion, wherein the head portion has a transverse cross sectional shape and a longitudinal cross sectional shape substantially the same as the transverse and longitudinal cross sectional curvature of the volar aspect of the distal radius.

11. The bone plate of claim 10 wherein the head portion includes a first plane generally defined by the head portion and the head portion includes a vertex portion defined by a junction of an distal end of the head portion and a first side edge, the vertex portion extending in a second plane so that the first and second plane form a first obtuse angle of about 150 degrees, and wherein the first obtuse angle faces in a direction generally opposite a second obtuse angle defined by a junction of the head portion and the elongate shaft portion.

* * * * *